United States Patent [19]

Olesen et al.

[11] Patent Number: Plant 6,860

[45] Date of Patent: Jun. 20, 1989

[54] ROSE PLANT NAMED POULLOW YELLOW HIT

[76] Inventors: Pernille Olesen; Mogens N. Olesen, both of Hillerodvej 49, DK 3480 Fredensborg, Denmark

[21] Appl. No.: 168,431

[22] Filed: Mar. 15, 1988

[51] Int. Cl.[4] ..... A01H 5/00

[52] U.S. Cl. ..... Plt./8

[58] Field of Search ..... Plt./8

*Primary Examiner*—James R. Feyrer

*Attorney, Agent, or Firm*—Vincent G. Gioia

[57] ABSTRACT

A new bright yellow miniature rose variety.

1 Drawing Sheet

The present invention relates to a new and distinct variety of rose plant of the miniature rose class, which was originated by my crossing as seed and pollen parents, unpatented, unnamed seedlings of my creation. The denomination of this new rose is "Poullow Yellow Hit".

Among the novel characteristics possessed by this new variety which distinguish it from its parents and all other varieties of which I am aware are its attractive bright yellow flowers that hold color well attractively displayed on plants that grow well in pots. Asexual reproduction by budding of the new variety as performed in Fredensborg, Denmark, shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Colour Chart (RHSCC). The terminology used in color description herein refers to plate numbers in the aforementioned color chart, e.g., "15C" is plate 15C of the Royal Horticultural Society Colour Chart.

Parentage: Seedling.

*Seed parent.*—My unpatented, unreleased, unnamed seedling.

*Pollen parent.*—My unpatented, unreleased, unnamed seedling.

Class: Miniature.

The following observations are made of specimens grown under glass in Fredensborg, Denmark during the month of October.

FLOWER

Blooming habit: Continuous.

A. Bud:

(1) *Size.*—Medium.

(2) *Form.*—Pointed, ovate.

(3) *Color.*—After sepals divide, near 15C.

(4) *Sepals.*—Substantially longer than bud, foliaceous.

(5) *Peduncle.*—Length — long, about $1\frac{1}{2}$ to $1\frac{3}{4}$ inch. Aspect — straight. Strength — erect. Color — green.

B. Bloom:

(1) *Size.*—Average size when fully expanded — about $1\frac{1}{2}$ to $1\frac{3}{4}$ inch.

(2) *Borne.*—Singly.

(3) *Form.*—Ovoid buds open flat, outer petals quill to points, inner petals roll under.

(4) *Petalage.*—Number of petals under normal conditions — about 20.

(5) *Color.*—The flower appears bright yellow near straw yellow 13C to chrome yellow 15C. Good yellow coloring holds well with some bleaching and lightening on outer petals as flowers mature. Petal undersurfaces are slightly lighter toned. Overall appearance is attractive bright yellow flower coloring.

C. Petals:

(1) *Texture.*—Thick, good substance.

(2) *Appearance.*—Inside velvety, outside satiny.

(3) *Form.*—Fan shaped.

(4) *Arrangement.*—Regularly arranged.

(5) *Petaloids in center.*—Few.

(6) *Persistence.*—Drop off cleanly.

(7) Fragrance.—Slight.

(8) *Lasting quality.*—Very long lasting quality on plant, indoors and outdoors.

REPRODUCTIVE ORGANS

A. Stamens, filaments and anthers:

(1) *Arrangement.*—Stamens regularly arranged around styles.

(2) *Color.*—Orange yellow.

B. Pollen:

*Color.*—Yellow.

C. Styles: Uneven length, spreading, few.

D. Stigmas:

*Color.*—Reddish.

Hips: None observed.

PLANT

A. Form: Compact, bushy.

B. Growth: Uniform branching.

*Height attained.*—About 7 to 10 inches in pots.

C. Foliage: Compound.

(1) *Size.*—Medium.

(2) *Quantity.*—Abundant.

(3) *Color.*—New foliage: Upper side — dark green with thin purple edges. Under side — light green. Old foliage: Upper side — dark green. Under side — lighter green.

(4) *Shape.*—Oval, pointed.

(5) *Texture.*—Upper side is semi-glossy and under side is matte.

(6) *Edge.*—Serrated.

(7) *Serration.*—Regular.

(8) *Leaf stem.*—Color — green. Under side — green.

(9) *Stipules.*—Medium.

(10) *Resistance to disease.*—Blackspot — very good. Mildew — very good. Rust — very good.

D. Wood:

(1) *New wood.*—Color — green with reddish tones. Bark — smooth.

(2) *Old wood.*—Color — green. Bark — smooth.

E. Thorns:

(1) *Thorns.*—Quantity (main stalk) — ordinary. On laterals from stalk — few. Form — thin, flat base. Length — short, narrow pointed. Color — light green. Position — regular.

(2) *Prickles.*—Profuse.

F. Winter hardiness: Winter hardy.

We claim:

1. A new and distinct variety of rose plant of the miniature rose class, substantially as shown and described, characterized particularly by bright yellow flowers which hold color well borne singly, one to a stem, attractively displayed against dark green foliage.

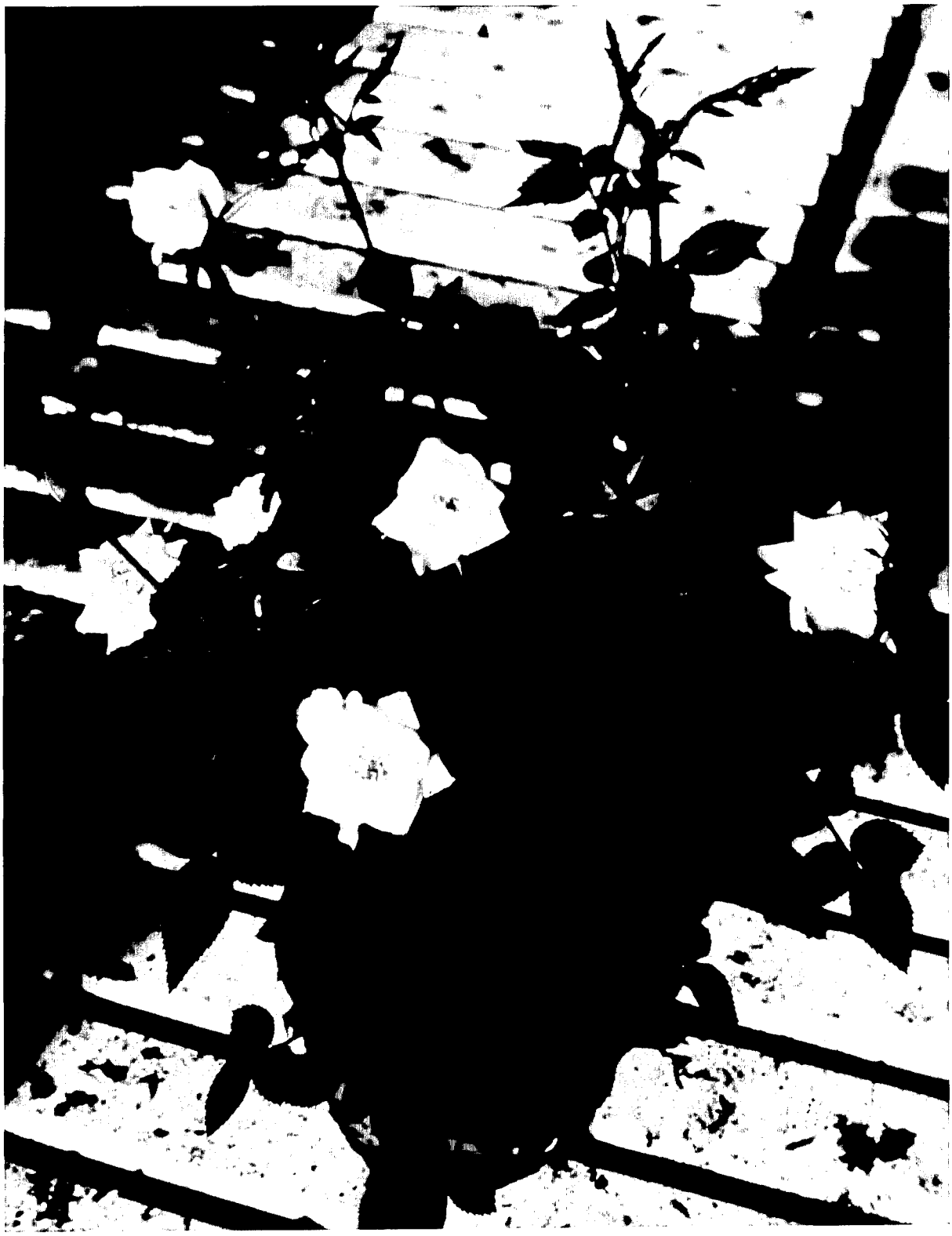

* * * * *